United States Patent [19]
Peuker et al.

[11] Patent Number: 6,105,761
[45] Date of Patent: *Aug. 22, 2000

[54] DEVICE FOR STORING AND DISPENSING A FLOWABLE SUBSTANCE

[75] Inventors: Marc Peuker, Seefeld; Mathias Bertl, Wildsteig; Dieter Poschmann, Starnberg, all of Germany

[73] Assignee: ESPE Dental AG, Seefeld, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/130,630

[22] Filed: Aug. 6, 1998

[30] Foreign Application Priority Data

Aug. 8, 1997 [DE] Germany ............ 297 14 246 U

[51] Int. Cl.⁷ .................................... B65D 69/00
[52] U.S. Cl. .................... 206/229; 206/15.3; 206/438
[58] Field of Search .................. 206/229, 230, 206/15.3, 361, 15.2, 570, 438, 63.5

[56] References Cited

U.S. PATENT DOCUMENTS

| | | | |
|---|---|---|---|
| 3,835,834 | 9/1974 | Brown et al. | 206/229 X |
| 4,844,251 | 7/1989 | Gueret | 206/229 X |
| 4,880,111 | 11/1989 | Bagwell et al. | 206/209.1 |
| 5,616,337 | 4/1997 | Kasianovitz et al. | 206/229 X |
| 5,660,273 | 8/1997 | Discko, Jr. | 206/229 |

FOREIGN PATENT DOCUMENTS

| | | |
|---|---|---|
| 0 049 553 | 7/1981 | European Pat. Off. . |
| 31 22 237 | 1/1983 | Germany . |
| 33 10215 | 9/1984 | Germany . |
| 37 17512 | 12/1987 | Germany . |
| WO 89 07053 | 8/1989 | WIPO . |

*Primary Examiner*—Jacob K. Ackun
*Attorney, Agent, or Firm*—Thomas J. Engellenner; Nutter, McClennen & Fish, LLP

[57] ABSTRACT

A device for storing and dispensing substances, preferably small quantities of liquids, including a container formed by two sheets, interconnected by hot sealing and cooperating to form a compartment for receiving the liquid and a pocket for receiving a brush. In the area between the compartment and the pocket, the connection between the sheets includes a pre-defined break zone which can be released by pressure exerted on the compartment, to force the liquid from the compartment into the pocket and wet the tip of the brush disposed therein.

21 Claims, 2 Drawing Sheets

DEVICE FOR STORING AND DISPENSING A FLOWABLE SUBSTANCE

BACKGROUND OF THE INVENTION

For storing and applying a small quantity of a liquid, a device is commercially available which includes a container in the form of a so-called "blister package". Two separate recesses are formed in the deep-drawn part of the package which is closed by a removable sheet. The first, smaller one of the recesses contains a quantity, e.g. 0.2 ml, of a liquid while the other, larger recess houses a brush. Upon removal of the sheet, the two container recesses are exposed so that the brush can be taken out and used to apply the liquid to the treatment site. The liquid is a dental substance for application in one single tooth treatment.

The stiff part of the blister package renders the known package comparatively bulky, which is undesired under storage and waste aspects; moreover, the package is relatively expensive to manufacture.

A further disadvantage of the known package resides in the fact that the brush and the liquid are accessible only after the flexible sheet has been removed from the stiff part of the blister package. The liquid is then exposed at a relatively large surface. Since the stiff part of the package is light and of little stability, there is the risk of the liquid being spilled due to careless handling, e.g. at the time when the brush is taken out.

EP 0 049 553 A1 discloses a package for separately storing two liquid components with a mixing instrument contained in the package. The package is made of two sheets that are sealed together at their edges, and the separation between the two container portions, each of which contains one component, is achieved by an externally applied clamping cleat. Upon removal of the cleat, the liquids are mixed by operating the instruments contained in the package. The finished mixture may be dispensed from a snout formed on the package. An application instrument is not disclosed.

WO 89/07053 discloses another device for storing and applying a liquid. A brush is disposed in a part of a cap which closes a liquid container. By removing the cap, the brush is accessible for applying the liquid. This arrangement is expensive and costly due to the large number of individual parts and the complicated shape of the cap. It is also for this reason, that the device is unsuited for small quantities of liquid used in a single working step.

A two-compartment container made of sheet material is known from DE 31 22 237 A1 wherein one compartment holds a liquid and the other holds part of a brush. The two compartments are always in communication with each other via a bore which extends through a shaft of the brush which is fixed in the device. For opening the container, the portion of the compartment surrounding the brush hairs is broken away, whereupon the remainder of the container forms an application brush with a handle containing a supply of the liquid.

DE 33 10 215 A1 shows an array of sheet containers disposed one behind the other, with each container having a compartment for holding a liquid and a handle with a blade provided therein. Upon tearing off a container, the blade contained in the handle of the next container slits open the compartment of the container being torn off. An application instrument is not provided.

DE 37 17 512 A1 discloses a three-compartment container of sheet material, wherein two of the compartments are disposed upon each other and contain two liquids to be mixed while the third compartment is disposed laterally and serves as a mixing compartment.

SUMMARY OF THE INVENTION

It is an object of the invention to provide a device for storing and dispensing quantities, particularly small quantities, of one or more flowable substances, which device should be as simple to handle as possible.

This object is achieved by a device for storing and dispensing a flowable substance comprising a container made of two sheets interconnected to form a compartment for storing a substance, a pocket for dispensing the substance, and a portion separating the compartment from the pocket, the separating portion including a passage area adapted to be selectively opened for placing the compartment in communication with the pocket.

In the device of the invention, the flowable substance, which may be a liquid or a powder, is made accessible without requiring any tool, by selectively opening the passage area, whereby the substance contained in the compartment is transferred to the pocket for dispensing. The structure of the invention acts as a metering device for dispensing and applying quantities of the substance which are determined by the volume of the compartment.

In a preferred embodiment, the pocket is formed so as to receive an application instrument. The application instrument, which is stored in a pocket of the container or is inserted into the same by the user, may be contacted with the flowable substance without opening the container as a whole. It is only necessary to withdraw the application instrument, after it has taken up the substance, from the pocket of the container and move it to the treatment site. Spilling of the substance will hardly occur even in careless handling.

Both of the sheets are preferably flexible, which is useful in that the container, being made of just two flexible sheets, is inexpensive in terms of material and manufacture. Using suitable sheets will safely avoid any diffusion of the compartment content. Thus, the sheet package may be used without any further envelope as a primary package which allows clear marking due to its flat and relatively large-area shape.

The separation between the compartment containing the flowable substance and the pocket receiving the application instrument is preferably achieved by mutual adherence of the two sheets. The adherence may be created simultaneously with the sealing of the compartment upon filling.

With a suitably selected size and strength of adherence between the two sheets, a pre-defined break zone is provided in order to constitute a connecting channel between the compartment and the pocket, on first use.

The sheets may be sealed together and the pre-defined break zone may be produced by using different sealing temperatures. Alternatively, particles which reduce the adherence between the sheets, specifically chips of a peel-off film, may be included between the sheets within the pre-defined break zone.

The pre-defined break zone may be opened either by pressure exerted on the compartment containing the substance or by an instrument, specifically the application instrument itself, inserted into the container pocket. This enables the user to put the device of the invention into use quickly and without problem.

To protect the substance contained in the compartment from light, the sheets may be sealed together by a pair of spaced seams surrounding the compartment.

In a preferred embodiment, the application instrument in its storage condition is received in the pocket and includes an outer portion projecting therefrom. The instrument is thus protected in the area which, in use, contacts the substance to be applied. At the same time, the pocket may be outwardly sealed by the application instrument, which has the additional effect that the instrument is secured against being lost.

The pocket formed in the deep-drawn sheet may include a trough portion extending outwardly beyond an outer edge of the cover sheet. The trough portion may advantageously serve as a dip-in cup so that the application instrument does not have to be re-inserted into the pocket, and wetting of its shaft is avoided. In addition, the edge clamps the shaft of the application instrument and prevents it from failing out of the pocket.

In a preferred embodiment, the device has two compartments for holding different substances with a passage area provided therebetween, which may be selectively opened for placing the compartments in communication with each other. This arrangement is specifically suited for substances to be mixed from components which react with each other. A zone of reduced lateral width may be provided between the compartments to facilitate the compartment which is emptied first to be bent upon the second compartment, thereby preventing the substance from flowing back into the first compartment.

A plurality of juxtaposed units may be formed in the sheets, each unit including a container and an application instrument, the units being inter-connected along tear-off lines. This embodiment results in a further simplification of the storage.

DETAILED DESCRIPTION OF PREFERRED EMBODIMENTS

Figure 1:
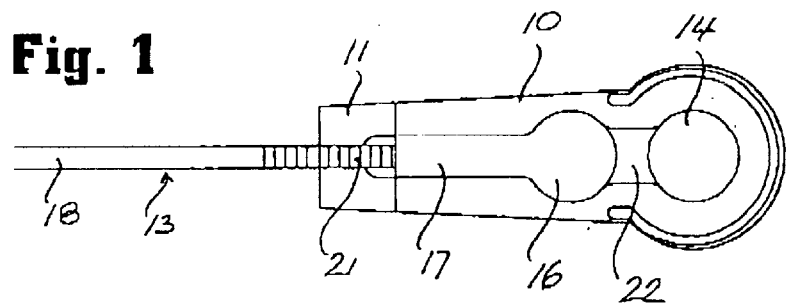
FIGS. 1 and 2 are a plane view and a sectional view, respectively, of a device for storing and dispensing a flowable substance in accordance with an embodiment of the invention.
Figure 2:
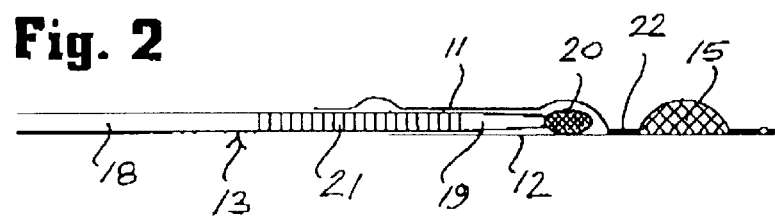

The storage and application device shown in FIGS. 1 and 2 consists of a container 10 formed by a deep-drawn sheet 11 and a cover sheet 12, and an application instrument in the form of a brush 13.

The sheets 11, 12 are formed with mutually adhering surfaces except in two areas. The deep-drawn sheet 11 is formed in one of these two areas with a cushion-shaped compartment 14 holding a supply of a flowable substance 15 and in the other area with a pocket 16 for receiving the brush 13. The pocket 16 includes a trough portion 17 which is not covered at its left-hand end in the drawings where the cover sheet 12 is shorter than the deep-drawn sheet 11. Alternatively, the trough portion may be formed in the cover sheet 12.

Tight mutual connection of the sheets 11, 12 is preferably achieved by hot sealing or gluing.

The sheets used are such that they act as a diffusion barrier with respect to the substance 15 to the received in the compartment 14. The deep-drawn sheet 11 is formed of a polypropylene layer, an aluminium layer, and a polyethylene layer, whereas the cover sheet 12 formed of a polyethylene terephthalate layer, an aluminium layer, and a polyethylene layer. In both sheets, a polyethylene terephthalate layer may be provided between the aluminium layer and polyethylene layers.

The shape of the compartment 14 may be generally circular as shown in the plan view in FIG. 1, or have any other geometric form. The pocket 16 for receiving the application instrument 13 is formed as a blind hole which, in the storing condition, terminates outside, but close to, the compartment 14. The compartment 14 and the pocket 16 are arranged with respect to each other preferably such that the axis defined by the pocket 16 and the trough portion 17 points to the center of the compartment 14.

The inner cross-section of the trough 17 is slightly larger than the outer diameter of the cylindrical brush shaft 18 so that in the storage condition illustrated in FIGS. 1 and 2 the front part of the shaft 18 is tightly received in the trough 17. In the embodiment shown, the shaft 18 has a conically tapering end 19, the ball-shaped enlarged tip portion 20 of which is fitted with radially extending brush hairs. The front part of the brush shaft 18 engaging the trough 17 is provided with peripheral ribs 21 to improve its grip.

In their peripheral portion surrounding the compartment 14, the sheets 11, 12 are interconnected by a pair of spaced seals to protect the substance 15 contained in the compartment 14 against light during storage.

The separation between the compartment 14 and the pocket 16 is designed with respect to spacing and strength of adherence between the sheets 11, 12 so that a pre-defined break zone 22 is created. With a view to minimum manufacture expenditure, the sheets 11, 12 are interconnected in the pre-defined break zone 22 by the same means as in the outer areas, e.g. by hot sealing or gluing. In case of sealing, the pre-defined break zone 22 may be produced by using a different, specifically a lower, temperature than in the outer connecting regions.

Another way of producing the pre-defined break zone 22 resides in including chips of a peel-off film or other foreign particles which reduce the adherence between permanent sealing sheets 11, 12.

Alternatively, the pre-defined break zone 22 may consist in a common embossing of the sheets 11, 12, a bend, a twist (similar to that at the ends of a candy package) or in a common application of several of these measures. It is further possible to achieve a separation between the compartment 14 and the pocket 16 by a clamp externally applied to the package for clamping the sheets 11, 12 in the region between the compartment 14 and the pocket 16.

In use, the two sheets 11, 12 are separated in the pre-defined break zone 22 to connect the compartment 14 with the pocket 16. This is preferably done by pressure on the cushion-shaped compartment 14, e.g. between the user's thumb and digit. Such pressure not only opens the pre-defined break zone 22 but at the same time reduces the compartment volume to cause the substance 15 to flow into the pocket 16 through the connection thus created, thereby wetting the brush tip 20 of the brush 13 which is in the pocket 16 already in the storage position or is inserted therein at this moment or later.

Alternatively, the brush 13 may be pressed toward the cushion 14 thereby releasing the pre-defined break zone 22 between the sheets 11, 12 and immersing the brush tip 20 into the flowable substance 15.

The wetted brush 13 is then moved to the treatment site to apply the substance 15. If the content of the pocket 16 is squeezed into the trough 17, the brush tip 20 may be re-wetted by simply dipping it in the exposed part of the trough 17 whereby the brush shaft 18 is prevented from being wetted also.

The device described above is particularly suitable for storing and dispensing small liquid quantities, such as dental substances which are required for a single application in amounts of few tenths of a milliliter. In such a case, the compartment 14 has a diameter of 10 to 15 mm in the embodiment shown, the brush 13 has a shaft diameter of about 2 mm, and the ball tip 20 carrying the brush hairs has a diameter of, e.g., 1 mm.

Figure 3:
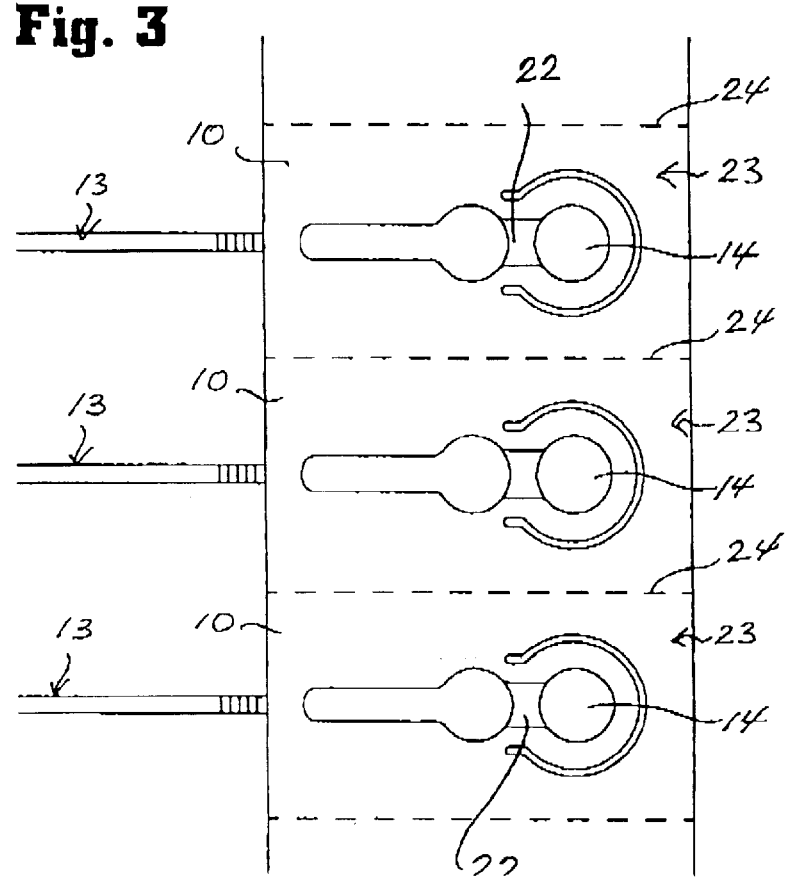
FIG. 3 illustrates a multiple-unit arrangement including a number of the devices shown in FIGS. 1 and 2, and FIGS. 4 to 6 are representations similar to FIGS. 1 to 3, showing an embodiment used for two-component substances.

In the embodiment shown in FIG. 3, the two sheets 11, 12 form a plurality of juxtaposed application units 23 each including a container 10 with a compartment 14 containing a quantity of a substance, and a pocket 16 containing a brush 13. The units are connected along tear-off lines 24.

The embodiment of FIGS. 1 to 3 relates to a one-component substance. The principle of the invention is likewise applicable to two- or multiple-component materials wherein each component is received in its own cushion-shaped compartment.

Figure 4:
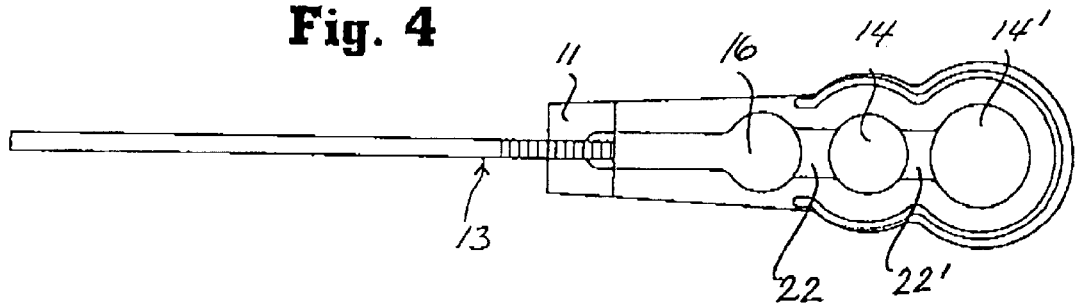
Figure 5:
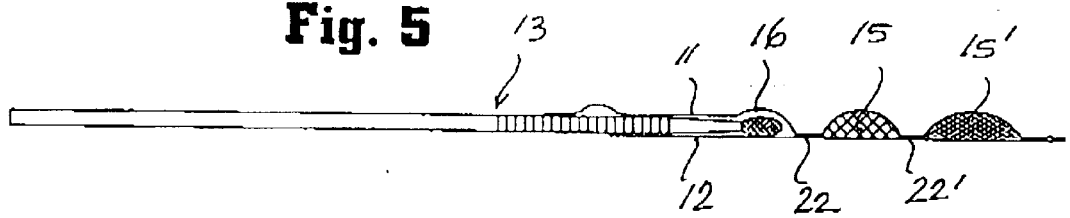
Figure 6:
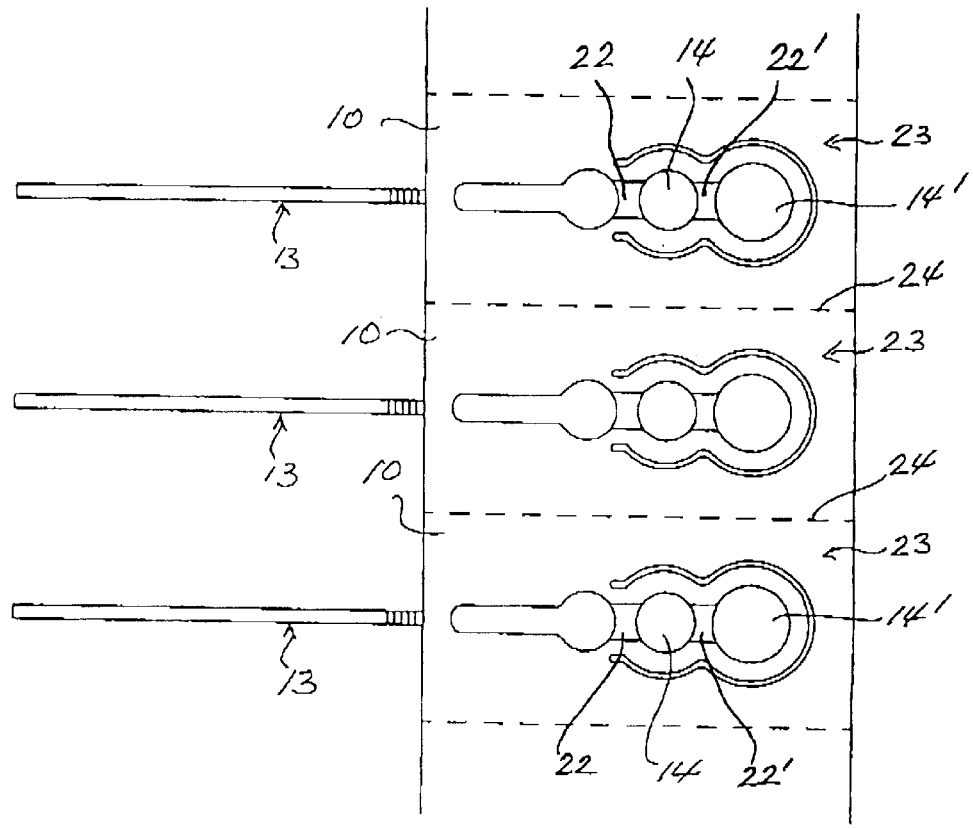

In the two-component embodiment of FIGS. 4 to 6, the device has two compartments 14, 14' separated from each other by a pre-defined break zone 22' in a manner similar to the separation between the compartment 14 and the pocket 16. Similar as in FIG. 1, the sheets 11, 12 are sealed together by a pair of spaced seams.

In use, pressure is first applied to the outer compartment 14' to connect it with the compartment 14 and mix the components 15, 15'. The part of the device comprising the emptied compartment 14' is then folded upon the compartment 14 such that the compartments 14, 14' contact each other at the side of the cover sheet 12. By exerting pressure on the compartment 14, the brush 13 is wetted with the liquid mixture. To make sure that the bending occurs at a proper location, the sheets 11, 12 are laterally recessed in the area between the compartments 14, 14'. Alternatively, both compartments may be pressed empty simultaneously. An additional mixing effect can be achieved by exerting pressure alternately on the compartments 14 and 14' after the pre-defined break zone 22' has been opened and before the pre-defined break zone 22 has been opened.

What is claimed is:

1. A device for storing and dispensing a flowable substance, comprising a container made of two sheets interconnected to form a compartment for receiving said substance, said compartment being sealed along its entire circumference, an open ended pocket for dispensing the substance, and a portion separating said compartment from said pocket, said separating portion including a passage area adapted to be selectively opened solely by pressure effective on said passage area for placing said compartment in communication with said pocket.

2. The device of claim 1, wherein said pocket is formed so as to receive an application instrument.

3. The device of claim 1, wherein both of said sheets are flexible.

4. The device of claim 1, wherein one of said sheets is a deep-drawn sheet formed of a polypropylene layer, an aluminum layer, and a polyethylene layer, and the other sheet is a cover sheet formed of a polyethylene terephthalate layer, an aluminum layer, and a polyethylene layer.

5. The device of claim 4, wherein a polyethylene terephthalate layer is disposed between said aluminum layer and said polyethylene layer of at least one of said sheets.

6. The device of claim 3, wherein said sheets are adhered to each other in forming said separating portion between said compartment and pocket.

7. The device of claim 6, wherein said passage area is constituted by a pre-defined break zone in which the adherence between said sheets is reduced.

8. The device of claim 7, wherein said sheets are sealed together, the sealing temperature used to form said pre-defined break zone being different from that used elsewhere.

9. The device of claim 8, wherein the sealing temperature used to form said pre-defined break zone is lower than that used elsewhere.

10. The device of claim 7, wherein particles reducing the adherence between said sheets are included between said sealed sheets to form said pre-defined break zone.

11. The device of claim 10, wherein said particles are chips of a peel-off film.

12. The device of claim 7, wherein the adherence between said sheets in said pre-defined break zone is adapted to be released by pressure exerted on said compartment.

13. The device of claim 7, wherein the adherence between said sheets in the pre-defined break zone is adapted to be released by pushing an instrument into said pocket.

14. The device of claim 1, wherein said sheets are sealed together by a pair of spaced seams surrounding said compartment.

15. The device of claim 2, further comprising an application instrument which, in a storage condition, is received in said pocket and includes an outer portion projecting from the pocket.

16. The device of claim 15, wherein said pocket is sealed from the outside by said application instrument.

17. The device of claim 1, wherein one of said sheets is a deep-drawn sheet and the other sheet is a cover sheet, said pocket being formed in said deep-drawn sheet and including a trough portion extending outwardly beyond an outer edge of said cover sheet.

18. The device of claim 1, comprising two compartments for holding different substances, and a passage area adapted to be selectively opened for placing said compartments in communication with each other.

19. The device of claim 18, wherein a zone of reduced lateral width is provided between said compartments.

20. The device of claim 1, wherein a plurality of juxtaposed units are formed in said sheets, each unit including a container and an application instrument.

21. The device of claim 20, wherein said units are interconnected along tear-off lines.

* * * * *